United States Patent
DeFreez et al.

[19]

[11] Patent Number: 5,946,093
[45] Date of Patent: Aug. 31, 1999

[54] PARTICLE DETECTION SYSTEM AND METHOD EMPLOYING AN UPCONVERSION LASER

[75] Inventors: Richard K. DeFreez, Azalea; Valey F. Kamalov, Medford, both of Oreg.

[73] Assignee: Met One, Inc., Grants Pass, Oreg.

[21] Appl. No.: 09/136,800

[22] Filed: Aug. 19, 1998

[51] Int. Cl.⁶ .................................................. G01N 15/06
[52] U.S. Cl. ........................ 356/339; 372/22; 250/222.2
[58] Field of Search .................... 356/338, 339, 356/336, 337; 250/222.2; 372/51, 53, 107, 108, 22, 97

[56] References Cited

U.S. PATENT DOCUMENTS

| | | | |
|---|---|---|---|
| 4,544,274 | 10/1985 | Cremers et al. | 356/436 |
| 4,571,079 | 2/1986 | Knollenberg | 356/336 |
| 4,796,995 | 1/1989 | Satzman et al. | 356/368 |
| 5,530,709 | 6/1996 | Waarts et al. | 372/6 |
| 5,621,749 | 4/1997 | Baney | 372/69 |
| 5,642,193 | 6/1997 | Girvin et al. | 356/339 |
| 5,677,920 | 10/1997 | Waarts et al. | 372/6 |
| 5,682,397 | 10/1997 | Scheps | 372/22 |
| 5,726,753 | 3/1998 | Sandberg | 356/338 |
| 5,727,007 | 3/1998 | Smart et al. | 372/6 |
| 5,742,632 | 4/1998 | Barnes et al. | 372/68 |
| 5,864,399 | 1/1999 | Girvin et al. | 356/339 |

OTHER PUBLICATIONS

Bohren, Craig F., Huffman, Donald R., "Absorption and Scattering of Light by Small Particles," Wiley Science Paperback Series, Chapter 5, pp. 130–137.

"Upconversion fiber lasers now power in the visible," *Laser Focus World*, May 1998, pp. 15–16.

Möbert, A., Heumann, E., and Huber, G., "Green $Er^{3+}$:$YLiF_4$ upconversion laser at 551 nm with $Yb^{3+}$ codoping: a novel pumping scheme," *Optics Letters*, vol. 22, No. 18, Sep. 15, 1997.

*Primary Examiner*—Hoa Q. Pham
*Attorney, Agent, or Firm*—Stoel Rives LLP

[57] ABSTRACT

A particle detector (10, 12, 70) employs an upconversion laser medium (22, 72) to produce emission radiation (32) at an emission wavelength (56) that is less than the wavelength of the pumping radiation (26). The shorter emission wavelength (56) provides a significant increase in the scattering intensity ($I_{sc}$) detected by the particle detector (10, 12, 70), based on the equation $I_{sc}=I_o k/\lambda^4$, where $I_o$ represents the intensity of emission radiation (32), $\lambda$ represents the wavelength (56) of the emission radiation (32), and k represents a coefficient related to particle size. In addition, the emission wavelength (56) of the upconversion laser medium (22, 72) can be frequency doubled to excite biological chromophores such as tryptophan, NADH, and flavin compounds that absorb in the UV spectral range and emit fluorescence at longer wavelengths that can be discretely detected to determine the presence of biological particles.

33 Claims, 5 Drawing Sheets

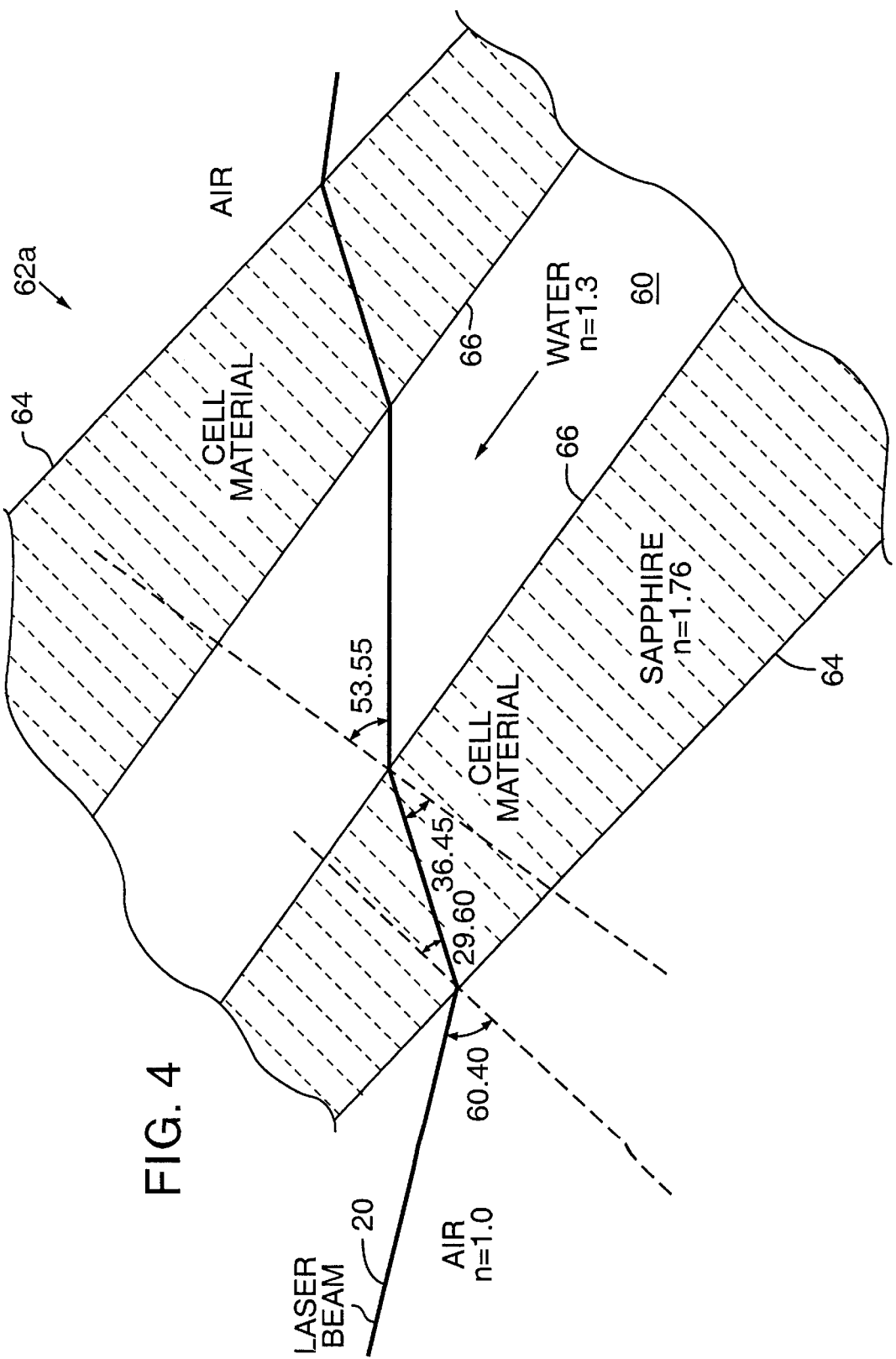

PARTICLE DETECTION SYSTEM AND METHOD EMPLOYING AN UPCONVERSION LASER

TECHNICAL FIELD

The present invention relates to optical detection of particles and, in particular, to a method and an apparatus employing an upconversion laser to increase the sensitivity of a laser-based particle detector.

BACKGROUND OF THE INVENTION

Contamination control, including particulate monitoring, plays a critical role in the manufacturing processes of several industries. These industries require cleanrooms or clean zones with active air filtration and require the supply of clean raw materials such as process gases, de-ionized water, chemicals, and substrates. For example, the Food and Drug Administration requires the pharmaceutical industry to monitor particulates because viable particles that contaminate products are closely correlated to detected particles in an aseptic environment. Semiconductor fabrication companies also require particulate monitoring as an active part of quality control. As integrated circuits become more compact, line widths decrease, and the sizes of particulates that cause quality problems become smaller.

Conventional optical particle detection relies on the direct detection of Rayleigh scattering of light by the particles (for particles that are small compared to the wavelength). Rayleigh light scattering intensity ($I_{sc}$) equals $I_o \, k/\lambda^4$, where $I_o$ represents an intensity of incident output radiation and $\lambda$ represents a wavelength of the incident output radiation. Particle size information is determined from the k coefficient based on the detected scattered intensity. Because light scattered by submicron particles is of small intensity, high incident intensity is necessary to achieve detectability. Therefore, to improve $I_{sc}$ measurements, the incident light intensity is preferably maximized by employing high intensity laser light. Because light intensity is higher inside a closed laser cavity, the incident light intensity is further increased by detecting intracavity light scattering. Unfortunately, optically pumped lasers conventionally used for particle detection generate an output wavelength that is longer than its pumping wavelength. This reduces the detectable Rayleigh scattering due to the inverse fourth power dependence of scattering intensity on the laser wavelength.

Although the wavelength from a "normal laser" can be converted in nonlinear crystal by harmonic generation, the efficiency of nonlinear conversion is limited. The efficiency of second harmonic generation depends on the intensity at the fundamental wavelength. Single pass conversion efficiency is typically far below 1% in the case of cw lasers of low intensity. Some applications (for example, biological particle characterization based on the measurement of protein autofluorescence) utilize UV light. Two nonlinear crystals have to be employed to generate the UV light whenever a conventional "normal" diode-pumped solid-state laser is the source of fundamental radiation. This results in even lower efficiency of nonlinear conversion. The employment of two nonlinear crystals also makes the laser system more complicated from a manufacturing and reliability standpoint.

Q-switched laser systems have been used for harmonic generation and subsequent particle characterization as taught by R. G. Pinnick, S. C. Hill, P. Nachman, G. Videen, G. Chen, R. K. Chang, *Aerosol Science & Technology*, v. 28, p. 95–104 (1998). Pulsed laser systems provide an easy technical solution for efficient generation of UV light in nonlinear crystals due to high peak power achievable in such lasers. Unfortunately, particles can be missed if traveling through the view volume between pulses. Therefore cw laser operation is preferred for particle counting.

SUMMARY OF THE INVENTION

An object of the present invention is to provide a particle detector with greater sensitivity.

Another object of the present invention is to provide such a particle detector that employs an upconversion laser.

Still another object of the present invention is to provide a particle detector that can also characterize a particle based on its response to radiation from an upconversion laser.

An advantage of such a upconversion laser-based particle detector is that it can be pumped by a relatively inexpensive and reliable diode laser for which power consumption is low.

Another advantage of such an upconversion laser-based particle detector is that it can employ a fiber laser that is compact and can substantially decrease the size of the particle detector.

Still another advantage of such an upconversion laser-based particle detector is that it can utilize second harmonic generation to excite fluorescence of biological chromophores.

Yet another advantage of a harmonically converted upconversion laser-based particle detector is that its fundamental and harmonic frequencies can simultaneously be employed for further characterization of particles based on their response to particular wavelengths of the upconversion laser.

The present invention provides a particle detector and counter that employs an upconversion laser to produce emission radiation at a wavelength that is less than the pumping wavelength. Upconversion lasers sequentially absorb two or more photons to convert low energy photons, such as infrared photons, to higher energy photons, such as visible photons, in a rare earth doped solid. Typically in upconversion lasers, the wavelength of the emission radiation equals the wavelength of the pumping radiation divided by 1.5 to about 2. Thus, for example, if the emission radiation has a wavelength that is one half the pumping radiation, then $I_{sc}$ will be enhanced by a factor of 16 over a system where the pumping radiation and emission radiation are at about the same wavelength. In normal lasers, where the wavelength of emission radiation is greater than the wavelength of pumping radiation, the scattering intensity is even lower so that the enhancement offered by the present invention is even more significant.

Additional objects and advantages of this invention will be apparent from the following detailed description of preferred embodiments thereof which proceeds with reference to the accompanying drawings.

BRIEF DESCRIPTION OF THE DRAWINGS

FIG. 4 shows an optical design for a Brewster cell to minimize reflections both at the air-cell and cell-water interfaces.

DETAILED DESCRIPTION OF PREFERRED EMBODIMENT

Figure 1:
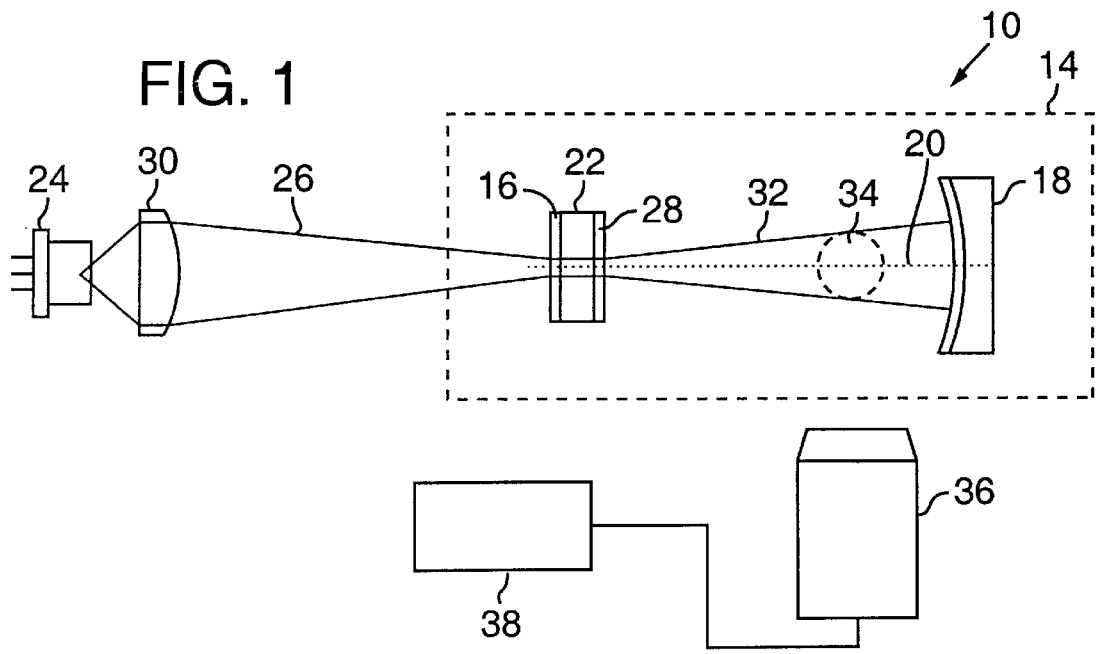
FIG. 1 shows a simplified plan view of an embodiment of a particle detector of the present invention designed to detect particles in air.
Figure 2:
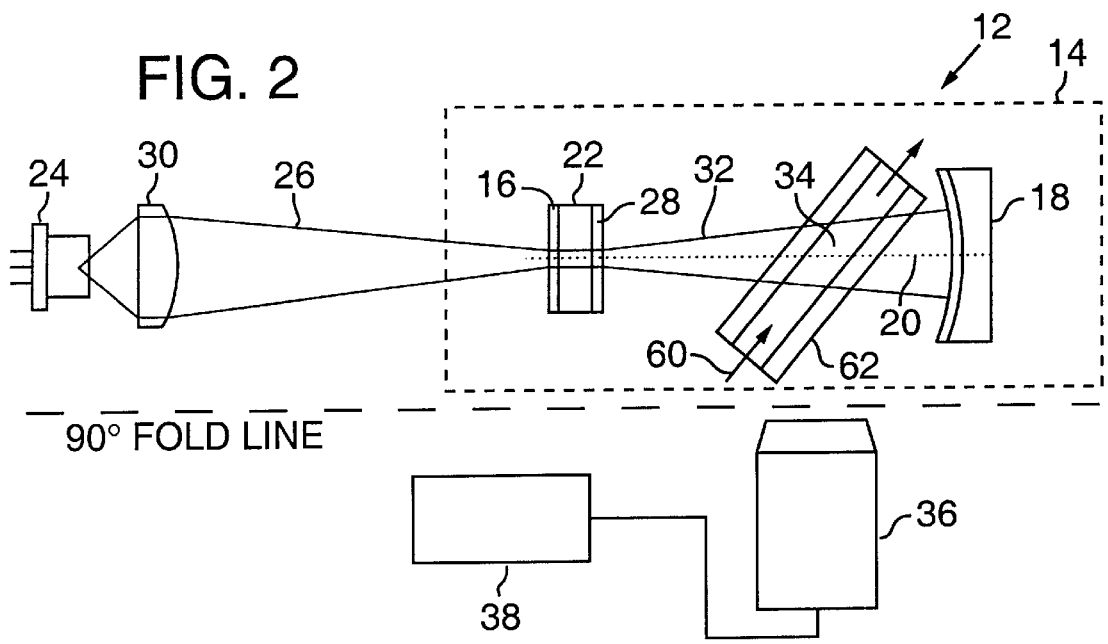
FIG. 2 shows a simplified plan view of an embodiment of a particle detector of the present invention designed to detect particles in deionized water.

FIGS. 1 and 2 show simplified plan views of respective embodiments of particle detectors 10 and 12 of the present invention for detecting particles in gas and liquid streams, respectively. For convenience, certain features common to particle detectors 10 and 12 of FIGS. 1 and 2, respectively, are designated with the same reference numbers.

With reference to FIGS. 1 and 2, particle detectors 10 and 12 include a resonator cavity 14 defined by two spaced-apart mirrors 16 and 18 positioned along an optical axis 20. An upconversion laser medium 22 is also positioned within resonator cavity 14 along optical axis 20 and between mirrors 16 and 18, which may be dielectric mirrors and are highly reflective to an upconversion wavelength 56 (FIG. 3B) of emission radiation 32 generated by laser medium 22. Furthermore, mirror 16 may be formed on or into the surface of laser medium 22 and is highly transmissive to the wavelength(s) 50 and 52 (FIG. 3B) of pumping radiation 26. Surface 28 of laser medium 22 preferably has an antireflection coating.

A pumping source 24 generates the pumping radiation 26, which is optically coupled through beam-shaping optics 30, into laser medium 22 to produce a beam of emission radiation 32 that propagates along optical axis 20. Emission radiation 32 could be Q-switched, but is preferably generated in continuous wave (cw) to avoid missing particles that could flow through view volume 34 during an interpulse period that would be created by the Q-switch. View volume 34 is positioned along optical axis 20 between mirror 18 and laser medium 22 and is generally defined by an intersection between a flow volume (not shown) and emission radiation 32. A fluid containing target particles is introduced into view volume 34 so that the emission radiation 32 can impinge upon the target particles and cause them to scatter light.

A detector 36 is disposed to sense light scattered from view volume 34 and produce signals proportional to the light that it senses. Typically, detector 36 is positioned to sense light scattered in a direction transverse to both optic axis 20 and a direction of fluid flow, and preferably perpendicular to them. A processing device 38, such as a pulse height analyzer, is in electrical communication to receive signals produced by detector 36 to quantitatively analyze the intensity of the light sensed to determine the number and size of particles in accordance with conventional analytical methods. This closed cavity system is highly efficient.

A suitable upconversion laser medium 22 includes an active laser ionic species that can sequentially absorb two more photons of a pumping radiation 26. Laser medium 22 preferably comprises a solid-state lasant in the form of a crystal or glass. The active laser ionic species is preferably a rare earth ionic species, such as $Tm^{3+}$ (thullium), $Er^{3+}$ (erbium), $Pr^{3+}$ (praseodymium) or $Ho^{3+}$ (holmium), because of the large number of intermediate metastable states available for upconversion of these species using the red or near infrared pumping wavelengths 50 and/or 52 of laser-diode-based pumping sources 24. For example, $Er^{3+}$ ions may be pumped at either 970 nm or 801 nm to produce 546 nm laser light. $Tm^{3+}$ ions may be pumped at 1120 nm to produce either 480 or 540 nm laser light. $Ho^{3+}$ ions may be pumped at 890 nm to produce 550 nm laser light. $Pr^{3+}$ ions may be pumped with both 835 nm and 1010 nm light to produce any of 520 nm, 491 nm, 605 nm or 635 nm laser light. Laser medium 22 may also be co-doped with other rare earth ionic species, which function as sensitizer ions facilitating the upconversion process. For example, a $Tm^{3+}$ lasant may be co-doped with $Nd^{3+}$ (neodymium) ions and pumped with 808 nm light, or co-doped with $Yb^{3+}$ (ytterbium) ions and pumped with 980 nm light, to produce 480 nm laser light. Likewise, $Ho^{3+}$ doped crystals or glass may be co-doped with $Yb^{3+}$ ions and pumped with 930 nm light to produce 550 nm laser light. Likewise, $Pr^{3+}$ doped crystals or glass can be co-doped with $Yb^{3+}$ ions and pumped with 840 nm light to produce 520 nm laser light. Likewise, $Er^{3+}$ doped crystals or glass can co-doped with $Yb^{3+}$ ions and pumped with 966 nm light to produce 551 nm laser light. Other ions, including $Nd^{3+}$, $Yb^{3+}$, and $Tb^{3+}$ (terbium) ions, with or without co-doping, are also possible upconversion laser active ions.

Figure 3A:
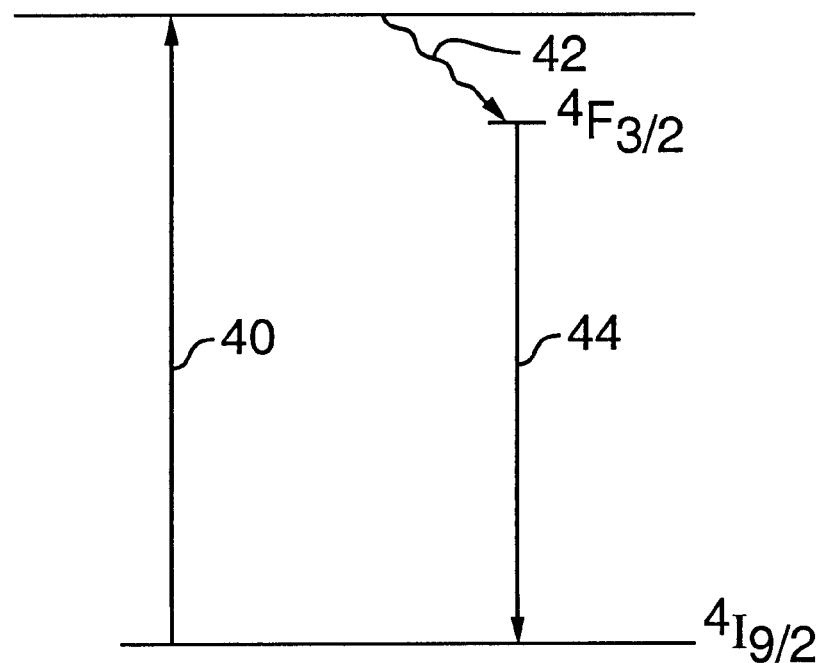
FIGS. 3A and 3B show energy level diagrams with absorptive and radiative transitions for exemplary "normal" and upconversion laser mediums, respectively.
Figure 3B:
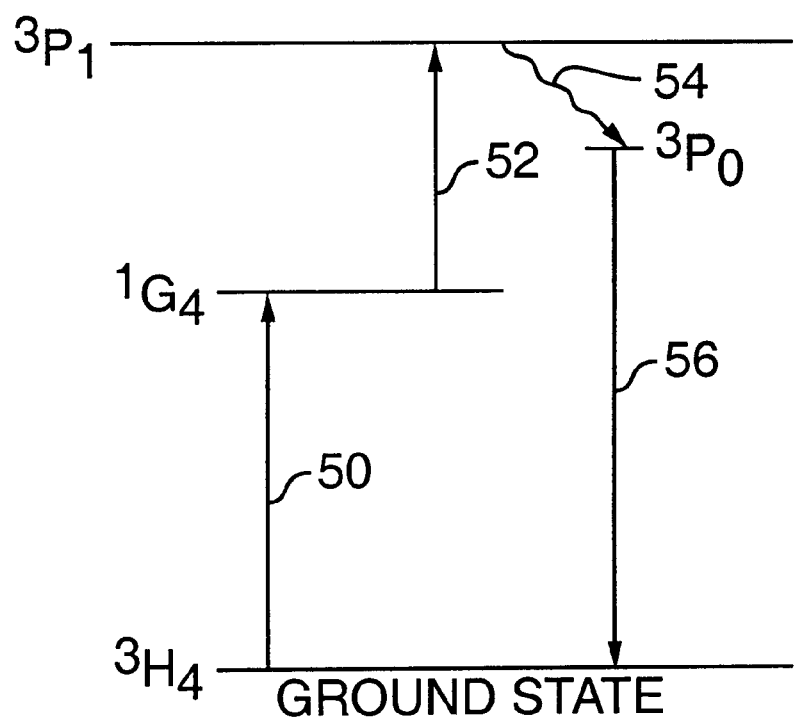

FIGS. 3A and 3B are energy-level diagrams showing absorptive and radiative transitions for an exemplary "normal" laser medium and an upconversion laser medium 22, respectively. With reference to FIG. 3A, a normal laser medium absorbs photons at a pumping wavelength 40, may undergo nonradiative decay 42 to a lower energy level, and during transition to the ground state emits lower energy photons at an emission wavelength 44 that is longer than the pumping wavelength 40. With reference to FIG. 3B, an exemplary upconversion laser medium 22 sequentially absorbs two photons at pumping wavelengths 50 and 52, may undergo nonradiative decay 54 to a lower energy level, and during transition to the ground state emits higher energy photons at an emission wavelength 56 that is shorter than the pumping wavelengths 50 and 52. Thus, with respect to the equation $I_{sc}=I_o k/\lambda^4$, particle detectors 10 and 12 employing upconversion laser mediums 22 will achieve a significant scattering intensity enhancement over particle detectors that employ normal lasers.

Particle detector 10 of FIG. 1 is preferably adapted for detecting particles in a gas and, particularly, in air. The direction and cross-sectional area of flow volume are generally determined by the aperture of an injection nozzle (not shown) and the flow pressure.

Particle detector 12 of FIG. 2 is preferably adapted for detecting particles in a liquid 60 and, particularly, in deionized water, flowing into view volume 34 through a sample cell 62. Deionized water exhibits small absorption in the visible spectral region, especially in the blue and green parts of the spectrum, so a sample cell 62 with deionized water introduced into resonator cavity 14 causes only small absorption losses and does not extinguish laser action. Losses due to reflections at surfaces 64 of sample cell 62 can be minimized by orientating sample cell 62 at the Brewster angle with respect to emission radiation 32 propagating along optical axis 20. In this embodiment, view volume 34 is defined by the intersection of emission radiation 32 with the flow volume within sample cell 62. Detector 36 senses the scattered light produced when the emission radiation 32 impinges on target particles within liquid 60.

Skilled persons will appreciate that sample cell 62 may be employed to facilitate detection of particles in a variety of liquids 60 employed in the manufacturing of pharmaceuticals, biologically-derived products, and semiconductors, as well as other products. Skilled persons will also appreciate that sample cell 62 can be employed to detect particles in gases that are different from the gas or gases in resonator cavity 14.

FIG. 4 shows a sectional view of an exemplary sample cell 62a optically designed to further decrease reflection losses at cell interfaces 64 and 66. With reference to FIG. 4, different Brewster angles for air-cell interfaces 64 and cell-water interfaces 66 are due to different ratios of refractive indices. The nonrectangular form of the cell window minimizes the reflections both at air-cell interfaces 64 and cell-water interfaces 66. Angles shown in FIG. 4 are calculated for a particular cell 62a made of sapphire, which has a refractive index of n=1.75, in a resonator cavity 14 filled with air, which has a refractive index of n=1.0, for liquid 60 of water, which has a refractive index of n=1.3. Skilled persons will appreciate that the angles of alternative cells 62a can be modified with respect to the refractive indices of other fluids, cell materials, and cavity gases.

Figure 5:
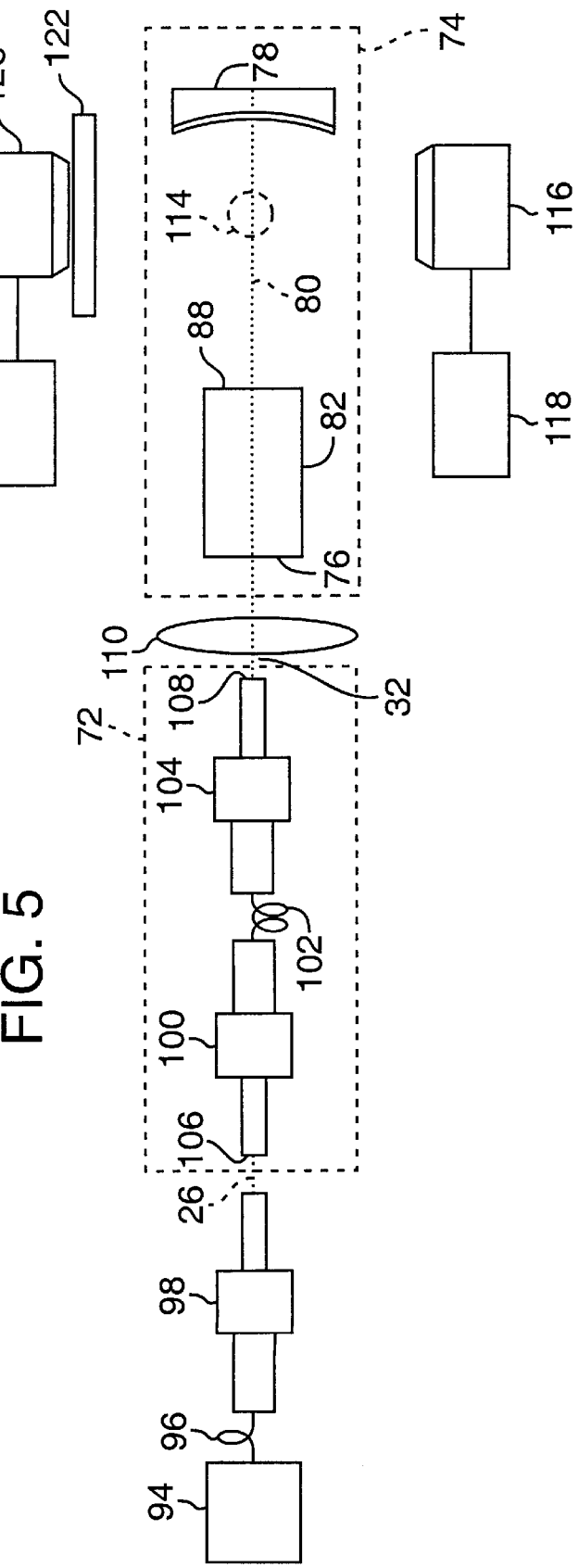
FIG. 5 shows a simplified plan view of an alternative embodiment of a particle detector of the present invention, preferred for detecting biological particles in a gas.

FIG. 5 is a simplified plan view of a preferred embodiment of a particle detector 70 adapted for detecting biological particles in a gas. With reference to FIG. 5, particle detector 70 includes an upconversion laser resonator 72 and an external resonator cavity 74 defined by two spaced-apart mirrors 76 and 78 positioned along an optical axis 80. A nonlinear optical crystal 82 is also positioned within external cavity 74 along optical axis 80 and between mirrors 76 and 78. Dielectric mirror 76 may be formed on the surface of nonlinear crystal 82 and is highly transmissive to the emission wavelength 56 of laser resonator 72 and highly reflective to the second harmonic of wavelength 56. Surface 88 of the nonlinear crystal 82 has an antireflection coating. A pumping source 94, such as a laser diode, generates pumping radiation 26 that is optically coupled through optical fiber 96 and its connector 98 into connector 100 and upconversion laser medium 102. Laser medium 102 is placed between mirror 106 and output coupler 108 to produce an emission radiation 32 that propagates along optical axis 80. The fundamental emission wavelength 56 of emission radiation 32 of the upconversion laser resonator 72 is preferably converted into the ultraviolet (UV) part of the spectrum by second harmonic generation in nonlinear crystal 82. Because conversion efficiency may be low, mirror 78 is preferably highly reflective to emission wavelength 56, as well as its second harmonic.

Mirror 106 may be formed on or into the surface of connector 100 and is preferably highly transmissive to the wavelength(s) 50 and 52 of pumping radiation 26 and highly reflective to the wavelength 56 of the emission radiation 32. Output coupler 108 may be formed on or into the surface of connector 104 and is partly reflective and transmissive to wavelength 56. Optical components 110 may optionally be positioned between laser resonator 72 and external cavity 74 to collimate or otherwise manipulate emission radiation 32.

A view volume 114 is positioned along optical axis 80 between mirror 78 and nonlinear crystal 82 and is generally defined by an intersection between flow volume and the cross-sectional area of the beam of UV radiation propagating along axis 80. A fluid, such as air, containing target particles is introduced into view volume 114 so that radiation 32 impinging upon the particles in view volume 114 produces scattered light. Skilled persons will appreciate that particle detector 70 may include a sample cell 62 or 62a, as shown in FIGS. 2 and 4 respectively, that overlaps view volume 114 to facilitate detection of particles in liquids or noncavity gases.

A detector 116 is disposed to sense light scattered from view volume 114 and produces signals proportional to the light sensed. Typically, detector 116 is positioned to sense light scattered in a direction transverse to both optic axis 80 and the longitudinal flow axis of the fluid through view volume 114, and preferably perpendicular to each. A processing device 118, such as a pulse height analyzer, is in electrical communication to receive signals produced by detector 116 to quantitatively analyze the intensity of the scattered light sensed. Skilled persons will appreciate that detector 116 can be adapted to detect light scattering at the fundamental emission wavelength 56 and/or at the harmonic wavelength. In this embodiment detecting scattered fundamental radiation is preferred due to low efficiency frequency conversion and the limited spectral sensitivity of photodiodes in the UV region.

In addition to elastic scattering, the UV wavelength can also be employed to detect the presence of biological particles that absorb UV light and emit fluorescence at a wavelength longer than that of elastically scattered UV light. The amino acids tryptophan, tyrosine, and phenylalanine absorb radiation in the 200–300 nm spectral region; reduced nicotinamide adenine dinucleotides (e.g., NADH and NADPH) absorb near 340 nm; and flavin compounds (e.g., FAD, FADH, riboflavin, flavoproteins) absorb near 450 nm. The amino acids generally emit at 300–400 nm; NADPH has an emission peak at about 470 nm; and flavin compounds emit near 540 nm. Thus, an additional one or more detectors 120 having broad spectral detection in the 300–550 nm range or specific wavelength detection ranges may be employed. These detectors are preferably photomultiplier tubes, but can be CCDs, or photodiodes.

Detector 120 is disposed to sense fluorescence emitted from view volume 114 and produces signals proportional to the light sensed. An optical filter 122, that cuts elastically scattered light but transmits light in the spectral region of protein fluorescence, is mounted in front of detector 120. Typically, detector 120 is positioned to sense fluorescence emitted in a direction transverse to both optic axis 80 and the longitudinal flow axis of fluid through view volume 114, and preferably perpendicular to each. A processing device 124, such as a pulse height analyzer, is in electrical communication to receive signals produced by detector 120 to quantitatively analyze the intensity of the fluorescence sensed.

Although particle detector 70 preferably employs an upconversion laser resonator 72 of a fiber laser design as shown in FIG. 5, skilled persons will appreciate that numerous alternative laser embodiments could be substituted and are contemplated. For example, a skilled person can adapt any of the embodiments of FIGS. 2–4 of U.S. Pat. No. 5,642,193 of Girvin et al. by substituting an upconversion laser medium 22 for Girvin's laser medium to achieve second harmonic generation. Moreover, nonlinear crystal 82 may be positioned within or external to the laser resonator 72, which can be tailored to be an open or closed cavity system. There may be advantages for inspecting the first and second harmonics together or separately.

Figure 6:
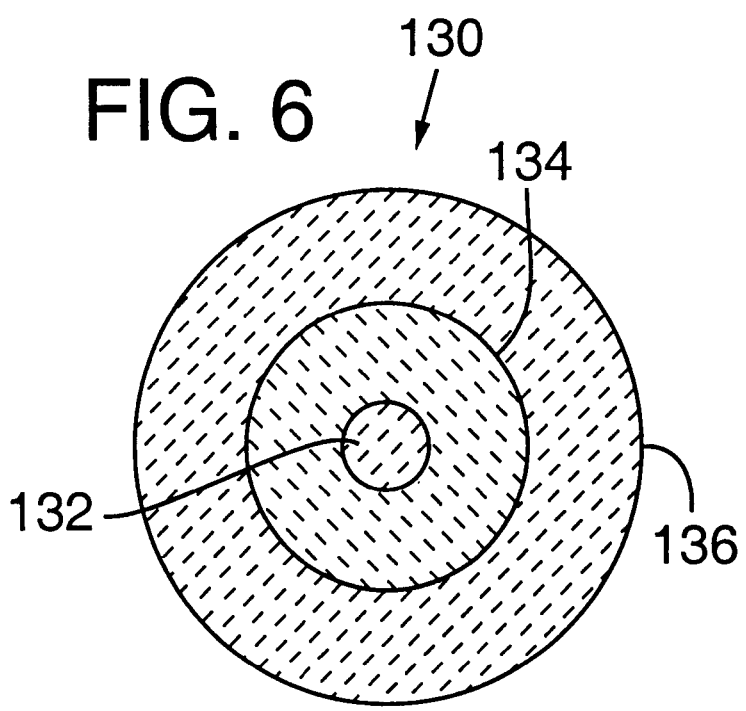
FIGS. 6 and 7 are sectional views of alternative optical fiber embodiments for use in the particle detectors of FIGS. 1, 2, and 5.
Figure 7:
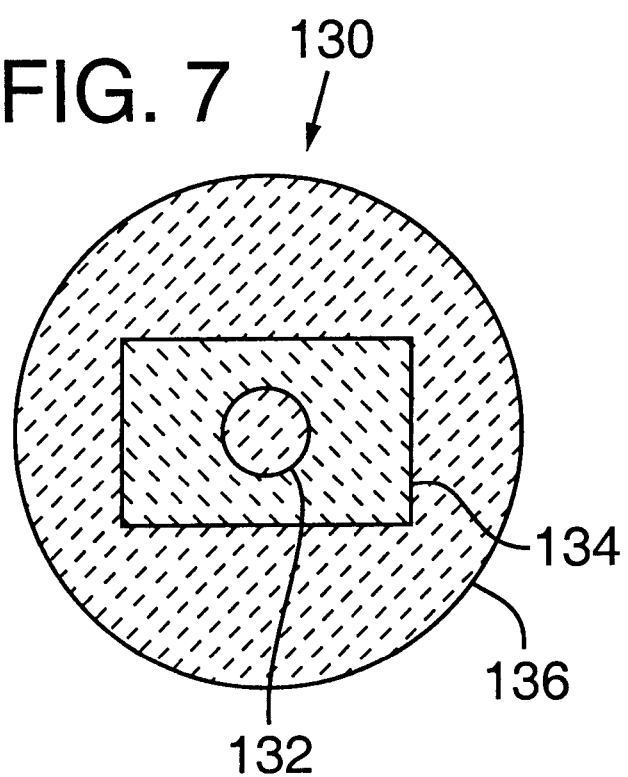

In a preferred embodiment, fiber lasants 102 are double-clad fibers 120, such as those illustrated in cross-section in FIGS. 6 and 7. The fiber core material serving as a host for the active laser ions is preferably a fluoride glass because of this material's long-lived intermediate states and broad pump absorption bands. The glass may be formed from a suitable mixture of some or all of $ZrF_4$, $HfF_4$, $BaF_2$, $SrF_2$, $LaF_3$, $YF_3$, $AlF_3$, KF, NaF, and LiF (or other suitable fluorides) in any combination. Fluorozirconate fibers (containing $ZrF_4$ as the primary ingredient), such as ZBLAN, are widely available in the fiberoptic telecommunications industry. The refractive index can be varied to produce the fiber cladding material by varying the compositional mix of the fiber, such as by adjusting the $ZrF_4/HfF_4$ ratio. While fluoride (especially fluorozirconate) fibers are preferred, other fiber materials, such as phosphate, silicate, borate and borosilicate glasses could also be used.

In FIGS. 6 and 7, a double-clad fiber 130 has a central core 132 doped with an active laser ionic species capable of undergoing upconversion excitation when optically pumped. The fiber 130 also has an inner cladding 134 surrounding the central core 132 with a lower refractive index than the central core 132 for substantially confining the laser light to the core 132. Surrounding the inner cladding 134 is an outer cladding 136 of still lower refractive index. The inner cladding 134 forms a low transmission loss waveguide for pumping radiation 50 and 52 emitted by the pumping source 94. The central core 132, forming the waveguide for the laser light generated therein, is a small diameter core which preferably supports only a single spatial mode of light propagation. The core diameter is generally at most 10 $\mu$m. The inner cladding 134 has an outer diameter which is typically in a range from 25 $\mu$m to 250 $\mu$m, and, together with the central core 132 which it surrounds, is capable of supporting multiple spatial modes of propagation of the pumping radiation. Pumping radiation propagating in the inner cladding 134 leaks into the higher index core 132 along the length of the fiber 130, which may be several meters long. The central core 132, inner cladding 134, and outer cladding 136 may have circular, elliptical, rectangular, or other geometrical cross-sections that may be the same, different, concentric, or off-axis. Some of these variations are described in U.S. Pat. No. 5,677,920 ('920 patent) of Waarts et al.

Skilled persons will appreciate that a variety of alternative pumping schemes can be employed. For example, pump light might be injected into the fiber 130 from both ends. The pump light injected into each end may be the same and comprise a broad spectral range or may be different, each specific to a different one of the two absorption wavelengths that promote upconversion in fiber 130. Alternatively, two pump sources may be coupled by means of a branching fiber connection. Certain of these and other possible laser embodiments are discussed in the '920 patent. Skilled persons will also appreciate that the nonlinear crystal 82 and view volume 114 may be alternatively positioned within laser cavity 72.

In a most preferred embodiment, fiber 130 is doped with active laser ionic species that permit it to generate emission radiation in the 540 to 650 nm range that can be harmonically converted to radiation in the 270 to 325 nm range that will cause biological chromophores, such as tryptophan, to fluoresce. Skilled persons will appreciate that numerous embodiments are possible utilizing the emission wavelengths of upconversion laser mediums, harmonic conversion, and the absorption ranges of specific biological particles.

It will be obvious to those having skill in the art that many changes may be made to the details of the above-described embodiment of this invention without departing from the underlying principles thereof. The scope of the present invention should, therefore, be determined only by the following claims.

We claim:

1. A particle detector employing an upconversion laser, comprising:

an upconversion laser medium doped with activator ions for generating emission radiation along an optical path in response to pumping radiation at a pumping wavelength, the emission radiation having an emission wavelength that is shorter than the pumping wavelength;

a resonator cavity defined by first and second spaced-apart reflective elements and including the laser medium positioned therebetween along the optical path;

a view volume intersecting the optical path, the view volume adapted for receiving a fluid containing target particles and exposing them to emission radiation propagating along the optical path such that the target particles scatter emission radiation impinging them; and a radiation-sensitive detector to detect radiation scattered by target particles in the view volume.

2. The particle detector of claim 1 in which the fluid comprises a liquid or a gas.

3. The particle detector of claim 1 in which the pumping radiation is generated by a diode laser.

4. The particle detector of claim 1 in which the upconversion laser medium comprises a crystal or glass with at least one of the following rare earth ions Er, Yb, Pr, Ho, or Tm.

5. The particle detector of claim 4 in which the upconversion laser medium comprises a fiber lasant.

6. The particle detector of claim 5 in which the upconversion laser medium comprises a double-clad fiber lasant.

7. The particle detector of claim 1 in which the upconversion laser medium comprises a fiber lasant.

8. The particle detector of claim 1 in which the view volume is positioned within the resonator cavity.

9. The particle detector of claim 8 in which a nonlinear crystal is positioned within the external cavity and is employed to convert the emission wavelength of the emission radiation to harmonic radiation at a harmonic wavelength of the emission wavelength.

10. The particle detector of claim 1 in which the view volume is positioned external to the resonator cavity.

11. The particle detector of claim 1 in which a nonlinear crystal is employed to convert the emission wavelength of the emission radiation to harmonic radiation at a harmonic wavelength of the emission wavelength.

12. The particle detector of claim 11 in which the harmonic radiation causes a compound indicative of a biological particle to fluoresce at a detectable wavelength.

13. The particle detector of claim 12 in which the compound comprises tryplophane, tyrosine, phenylalanine, a reduced nicotinamide adendine dinucleotide, or a flavin compound.

14. The particle detector of claim 11 in which the harmonic radiation comprises a wavelength within the 250–540 nm spectral range.

15. The particle detector of claim 1 in which the emission radiation comprises continuous wave emission.

16. A method for increasing the sensitivity of a particle detector that detects scattering intensity ($I_{sc}$) of emission radiation generated from a laser medium and provides particle sizing information generally based on an equation: $I_{sc}=I_o k/\lambda^4$, where $I_o$ represents an intensity of the emission radiation, $\lambda$ represents an emission wavelength of the emission radiation, and k represents a coefficient related to particle size, comprising:

directing pumping radiation at a pumping wavelength into an upconversion laser medium in a resonator cavity;

generating along an optical path emission radiation at the emission wavelength from the upconversion laser medium, the emission wavelength being shorter than the pumping wavelength;

introducing, into a viewing volume positioned along the optical path, target particles suspended in a fluid;

directing the emission radiation through the viewing volume to impinge the target particles and cause them to scatter a portion of the emission radiation;

detecting the $I_{sc}$ of the scattered radiation to determine the sizes of the target particles.

17. The method of claim 16 in which the upconversion laser medium comprises a crystal or glass with at least one of the following rare earth ions Er, Yb, Pr, Ho, or Tm.

18. The method of claim 17 in which the upconversion laser medium comprises a fiber lasant.

19. The method of claim 18 in which the upconversion laser medium comprises a double-clad fiber lasant.

20. The method of claim 19 in which the view volume is positioned external to the resonator cavity.

21. The method of claim 20 in which a nonlinear crystal is positioned within the external cavity and is employed to convert the emission wavelength of the emission radiation to harmonic radiation at a harmonic wavelength of the emission wavelength.

22. A biological particle detector employing an upconversion laser, comprising:

an upconversion laser medium doped with activator ions for generating emission radiation along an optical path in response to pumping radiation at a pumping wavelength, the emission radiation having an emission wavelength that is shorter than the pumping wavelength;

a resonator cavity defined by first and second spaced-apart reflective elements and including the laser medium positioned therebetween along the optical path;

a nonlinear crystal positioned along the optical path to convert the emission radiation to harmonic radiation at a harmonic wavelength of the emission wavelength;

a view volume intersecting the optical path, the view volume adapted for receiving a fluid containing biological particles and exposing them to harmonic radiation propagating along the optical path such that the biological particles absorb the harmonic radiation impinging them and emit fluorescence radiation at a fluorescence wavelength different from the harmonic wavelength; and a wavelength-sensitive radiation detector to detect fluorescence radiation emitted by biological particles in the view volume.

23. The particle detector of claim 22 in which the upconversion laser medium comprises a crystal or glass with at least one of the following rare earth ions Er, Yb, Pr, Ho, or Tm.

24. The particle detector of claim 22 in which the upconversion laser medium comprises a fiber lasant.

25. The particle detector of claim 22 in which the upconversion laser medium comprises a double-clad fiber lasant.

26. The particle detector of claim 22 in which the view volume is positioned within the resonator cavity.

27. The particle detector of claim 22 in which the view volume is positioned external to the resonator cavity.

28. A method for detecting the presence of a biological particle, comprising:

directing pumping radiation at a pumping wavelength into an unconversion laser medium in a resonator cavity;

generating emission radiation from the upconversion laser medium along an optical path at the emission wavelength, the emission wavelength being shorter than the pumping wavelength;

converting the emission radiation to harmonic radiation at a harmonic wavelength of the emission wavelength;

introducing, into a viewing volume positioned along the optical path, biological particles suspended in a fluid;

directing the harmonic radiation through the viewing volume to impinge the biological particles such that the biological particles absorb the harmonic radiation impinging them and emit fluorescence radiation at a fluorescence wavelength that is different from the harmonic wavelength; and detecting the fluorescence wavelength to determine the presence of the biological particles.

29. The method of claim 28 in which the upconversion laser medium comprises a crystal or glass with at least one of the following rare earth ions Er, Yb, Pr, Ho, or Tm.

30. The method of claim 28 in which the upconversion laser medium comprises a fiber lasant.

31. The method of claim 28 in which the upconversion laser medium comprises a double-clad fiber lasant.

32. The method of claim 28 in which the view volume is positioned within the resonator cavity.

33. The method of claim 28 in which the view volume is positioned external to the resonator cavity.

\* \* \* \* \*